United States Patent [19]

Poulmaire

[11] Patent Number: 5,246,369
[45] Date of Patent: Sep. 21, 1993

[54] IMPLANTABLE SYSTEM, ROTARY DEVICE AND OPERATING METHOD

[76] Inventor: Francis Poulmaire, 23, rue de la Republique, F-8400 Avignon, France

[21] Appl. No.: 656,185
[22] PCT Filed: Sep. 4, 1989
[86] PCT No.: PCT/FR89/00443
   § 371 Date: May 15, 1991
   § 102(e) Date: May 15, 1991
[87] PCT Pub. No.: WO90/02529
   PCT Pub. Date: Mar. 22, 1990

[30] Foreign Application Priority Data
   Sep. 2, 1988 [FR] France ............... 88 11615

[51] Int. Cl.$^5$ .................................. A61C 8/00
[52] U.S. Cl. ........................... 433/173; 433/174
[58] Field of Search ........... 433/173, 174, 175, 176, 433/177, 169

[56] References Cited

U.S. PATENT DOCUMENTS

| | | | |
|---|---|---|---|
| 4,185,383 | 1/1980 | Heimke et al. | 433/173 |
| 4,447,209 | 5/1984 | Sutter | 433/173 |
| 4,552,532 | 11/1985 | Mozsary | 433/173 |
| 4,746,293 | 5/1988 | Lundgren et al. | 433/173 |
| 4,957,437 | 9/1990 | Shimura et al. | 433/174 X |
| 4,960,381 | 10/1990 | Niznick | 433/173 X |
| 5,006,068 | 4/1991 | Lee et al. | 433/169 |
| 5,026,280 | 6/1991 | Durr et al. | 433/173 X |
| 5,040,982 | 8/1991 | Stefan-Dogar | 433/169 |
| 5,049,073 | 9/1991 | Lauks | 433/173 |
| 5,071,351 | 12/1991 | Green, Jr. et al. | 433/173 |

FOREIGN PATENT DOCUMENTS

| | | | |
|---|---|---|---|
| 2413883 | 9/1975 | Fed. Rep. of Germany | 433/173 |
| 2214087 | 8/1989 | United Kingdom | 433/173 |

Primary Examiner—Gene Mancene
Assistant Examiner—Nicholas D. Lucchesi
Attorney, Agent, or Firm—Harrison & Egbert

[57] ABSTRACT

A resilient or non-resilient implantable system which is either screwed on and self-tapping or impacted, depending on the bone site to be exploited, and which is used to replace a dental organ. The system is comprised of an implant body and of an implant head. It consists of a cylindrical tube having in its upper part a threaded shaft combined with an asymmetrical hexagonal socket and in its lower part a hollowed-out portion occupying the entire width of the cylindrical tube and the maximum of the height comprised between the bottom of the internal threading and the apex part of the cylindrical tube. The vertical edges of the hollowed-out part of the cylindrical tube consist in flat surfaces. The external surface of the cylindrical tube, is provided with an external threading with a thread of no less than 1.25 mm. For the self-tapping implant to be screwed on as well as for the impacted implant, the external threading is advantageously constituted by a series of shoulders which are superposed so as to permit the implant body to be impacted when it cannot be screwed. The invention also relates to a combination of the body with a resilient implant head having at least two shock-absorbing elements, to the rotating material for housing the system and to a method for using the system. The resilient head can be adapted to fit complete implants, designed for toothless people, and juxta-osseous implants.

10 Claims, 6 Drawing Sheets

FIG. 12 ically.

IMPLANTABLE SYSTEM, ROTARY DEVICE AND OPERATING METHOD

TECHNICAL FIELD

This invention relates to an implant, either resilient or resilientless system, screwed with self-cutting ability or impacted, to be used as a substitute for a dental organ, a rotary device for designing the implantary seating, the operating method of such rotary device and the operating method of said implantable system.

BACKGROUND ART

Implants typically behave as inert bodies within the maxillaries. When the implants revert to the osseous cells a gradual thickening of the proteoglycans layer occurs. This can induce the growth of neo-forming fibrous or bony tissues.

Moreover, the clinical experience shows that the prosthetic arrangement combining a resilient less artificial implantary post with the natural and resilient dental abutment generates prothesis loosening and even breaking either at implantary posts level or at natural abutments level.

In other terms, the practitioners now have available implants made of titanium, aluminium oxyde or any other biomaterials, such implants supporting unitary prosthesis, i.e. bridges or associated prosthesis.

The system implementation causes more or less shortly the bone lysis and replacement by atypical tissue.

Such degeneration is mainly due to the absence of the implantary-alveolo ligament opposing the impacts conveyed by the mandible or the maxillary during the mastication, swallowing and even the phonation.

In spite of numerous attemps for improvement, the present systems do not elude these numerous drawbacks, i.e.:
widespread destruction of the receiving jawbone,
thermal necrosis though heating of the drilling tool,
bone/implant interface insufficient to balance the mechanical strengths.

The object of this invention is to remedy such drawbacks by providing an implantable system that exhibits the double advantage of combining thoroughly with the jawbone and of securing a "physiological mobility" similar to that of the dental organ. Obviously, the dental prosthesis life will last markedly longer.

Another object of this invention is to remedy the thermal necrosis due to the osseous cells overheating by providing an implementary seating intended to receive said implantable system using a rotary device with internal irrigation.

The seating thus obtained can receive either a screwed and self-cutting implant, in the case of thick, bony walls, withstanding the cutting strengths or an impacted implant in the case of narrower bony walls.

SUMMARY OF THE INVENTION

To this end, the first object of the invention is to provide an implantable system for supporting a dental prosthesis of the type including on one hand an implant body consisting of a solid cyclindrical tube provided with an internal threading connected to the upper opening of said implant body combined with an asymmetrical hexagon socket mechanism.

The presence of an asymmetric hexagon mechanism combined with the internal threading of said implant body enables on one hand to place a device for positioning the implant inside the bone and on the other hand to screw and seal prosthetic inserts consequently.

The hexagon asymmetry ensures that on handling by the prosthesis laboratory the correct position of the prosthetic insert will be found.

The implant body includes in its largest lower portion a recess extending across the width of said implant body and the maximal height between the bottom portion of said internal threading combined with the asymmetric hexagon mechanism and the apical portion of said cylindrical tube, thus forming two communicating openings arranged oppositely along the said cylindrical tube, each vertical edge of this recessed portion being in the form of a side face.

A maximal gap arrangement inside said implant body through the large emptied portion aims at providing a minimal metallic mass available within said implantary seating while the maximal gap is to be filled in with osseous regeneration during the bone cicatrization.

The presence of said side faces is intended to achieve the said implant body keying inside the osseous tissues.

Thus, the said implant body will have the form of a cylinder provided with an external threading the said external threading of said cylindrical tube will have a thread of at least 1.25 mm.

The said body implant will be screwed accordingly and owing to a slight oversizing a self-cutting ability will be achieved.

A further advantage of this invention lies in that the external threading of the implant body may be comprised of a number of shoulders lying on another. By this way, the implant is impacted in the jaw directly, should the bone not be sufficient to allow screwing.

In one preferred embodiment of the invention, the said implant body is combined with an implant head provided with at least two shock-absorber units acting as a resilient device so as to compensate the lack of alveolo-implantary ligament and thus minimize the contrary effects due to mechanical stresses.

As described before, the invention provides either a resilientless implantable system, solely achieving the implant body perfect integration to the implantary seating or a resilient implantable system the resilience thereof achieved through the presence of at least two shock-absorber units along the said implant head.

Another feature of this invention lies in the design of the implantary seating to be realized prior to the screwing of said implant body. As a matter of fact, the osteogeny to be practised inside the recessed section requires the presence of osseous cells within the implantary seating both vivid and capable of regeneration. Now, usual drilling processes do provoke an overheating of the osseous cells up to 70° C. thus entailing non-reversible lesions.

Consequently, this invention provides a rotary device intended for the design of a cylindrical implantary seating comprised of a drill including an internal irrigation channel.

The drill allows the bone and osseous site to be drilled directly with no risk of being overheated; it includes a system providing therein an abundant, central irrigation. On drilling of the said implantary seating which is intended to accommodate said implant body, a freezing cooling liquid free from germs is sent through said irrigation channel of the rotary device while the rotating speed during the drilling is very slow, i.e. approximately 400-500 rpm.

Finally, another object of this invention is to provide an operating method for the implantable system.

According to a first embodiment, with a screwed and self-cutting implant:

within the hexagon threaded socket of said implant body is positioned a male hexagon drill chuck.

Thereafter, said drill chuck is actuated by using a ratchet handle so as to complete the implant screwing. Marks on the hexagon drill chuck facilitates the locating of the vent orientation of said implant body in the anteroposterior direction with respect to the jawbone.

According to a second embodiment, with an impacted type implant:

the use of an impacter, metallic rod the end of which enters in the pit of the implant body and is to be provided with a shock-absorbing material (very soft strokes given with a surgical hammer will bring the implant to the bottom of the implantary seating).

In both cases an implant head is to be screwed within the upper opening of said implant body, said dental prosthesis being secured thereon.

Further advantages and embodiments of the invention will be apparent from the following description with reference to the accompanying drawings in which:

BRIEF DESCRIPTION OF THE DRAWINGS

FIGS. 10(a)-10(e) show an overall view and a sectional view A—A of the rotary device according to the invention;

DETAILED DESCRIPTION OF THE INVENTION

Figure 9:
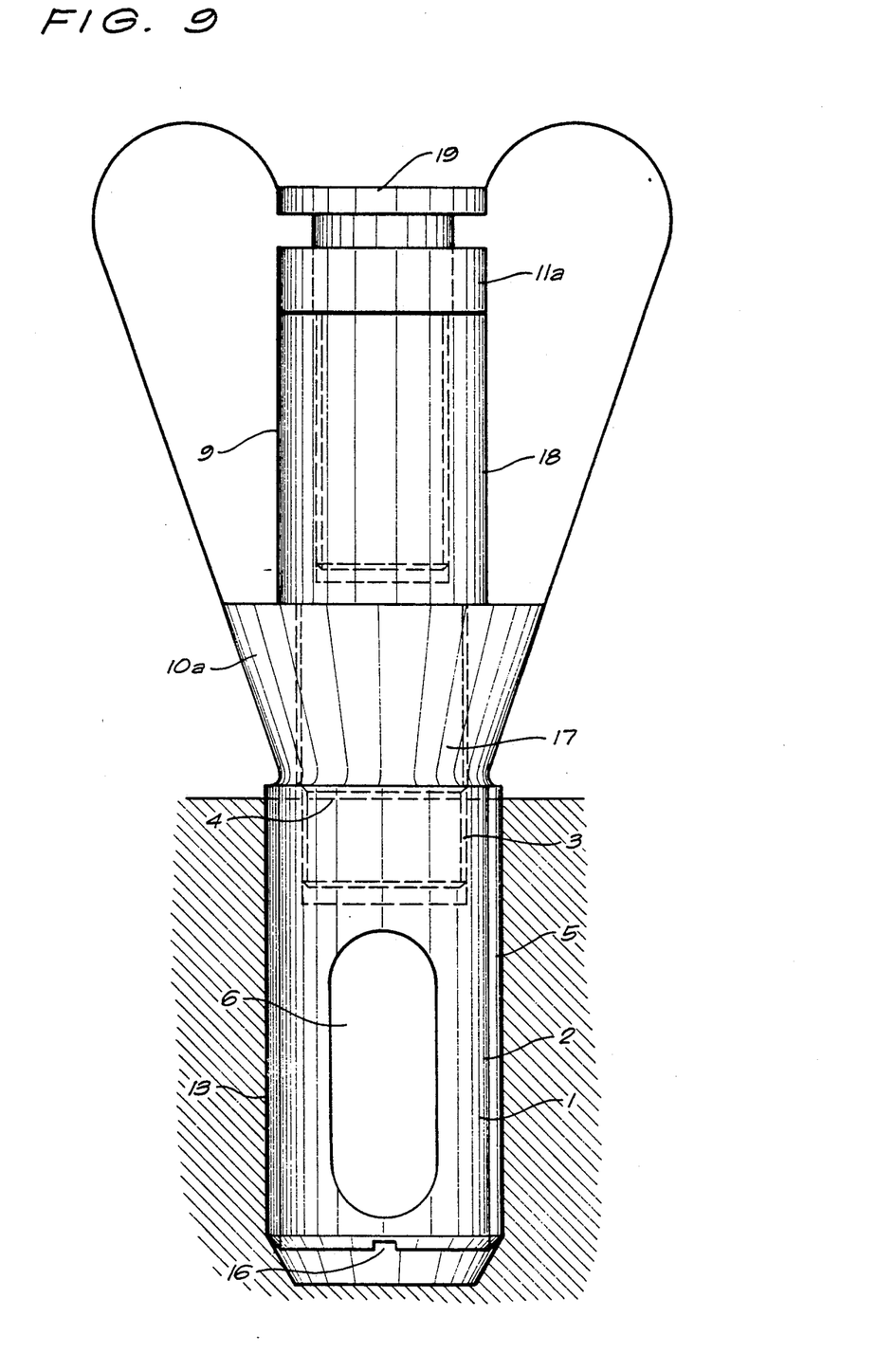
FIG. 9 is a view of the implantable system as implemented with the dental prosthesis.

As illustrated in FIG. 9, the implantable system for supporting a dental prosthesis according to the invention, of the type including an implant body (1) composed of a solid cylindrical tube (2) provided with an internal threading (3) in its upper opening (4) combined with an hexagon socket mechanism (10) as well as an external threading (5). FIG. 9 illustrates the manner in which the screwed implant (of FIGS. 1 and 2) can be used. The screwed implant has a thread having a size of at least 1.25 mm. FIG. 9 also illustrates the manner in which the impacted implant embodiment of FIGS. 3 and 4 can be used. When the impacted implant is used, the implant settling within the jawbone is achieved through an impacting due to the embossing of said shoulders (12). This way, the biasing of the implantary seating walls will be reduced thus avoiding the jawbone embrittlement or cracking.

Figure 1:
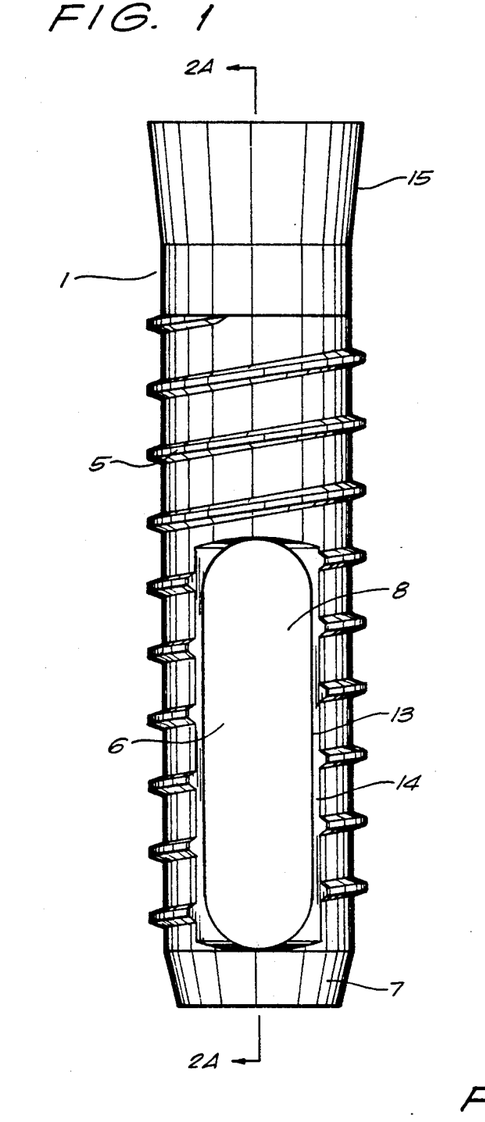
FIG. 1 is an overall view of the implant body screwed in accordance with this invention.
Figure 2A:
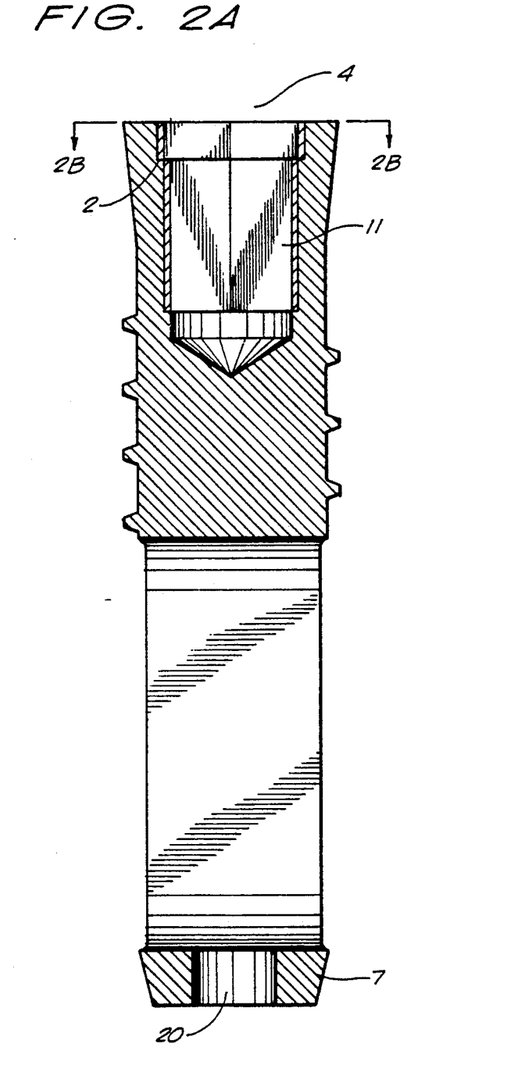
FIG. 2 is a cross-sectional view taken along axis A—A of FIG. 1.
Figure 2B:
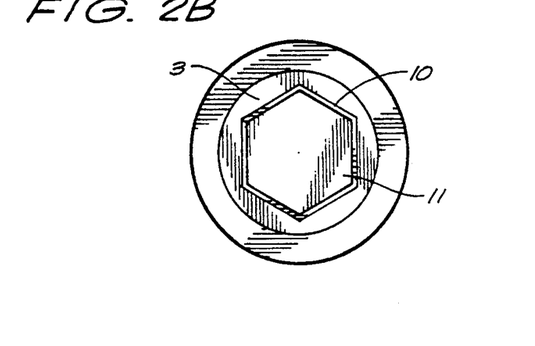

Referring to FIGS. 1 and 2, if an implant head is to be screwed or sealed into said internal threading (3) of the implant body (1), then said cylindrical tube (2) comprises a recessed section (6) extending across the whole width of said cylindrical tube (2) and the maximal height between the bottom of said internal threading (3) and the apical section (7) of said cylindrical tube (2). Two openings (8) communicate and stand oppositely along said tube (2).

These two communicating openings are limited by vertical edges (13), as the latter might have formed irritating sections with regard to the biological environment. The vertical edges (13) of the communicating openings (8) are provided with side faces (14). In this manner, the vertical edges (13) do no longer rasp the osseous wall and the osteogeny is achieved by the coagulum present inside the recessed portion (6), exclusively.

Moreover, this recessed portion (6) is communicating with the bottom of the implantary seating through a decompression hole (20) which is formed at the level of the apical portion (7) of said implant body so as to facilitate the entry of the clump into the recessed portion (6).

Figure 3:
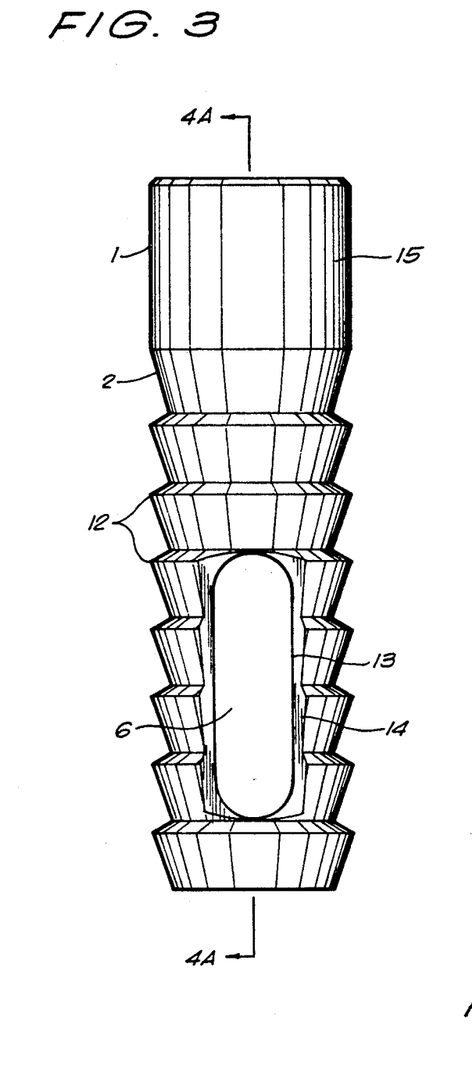
FIG. 3 is an overall view of the implant body impacted in accordance with the invention.
Figure 4A:
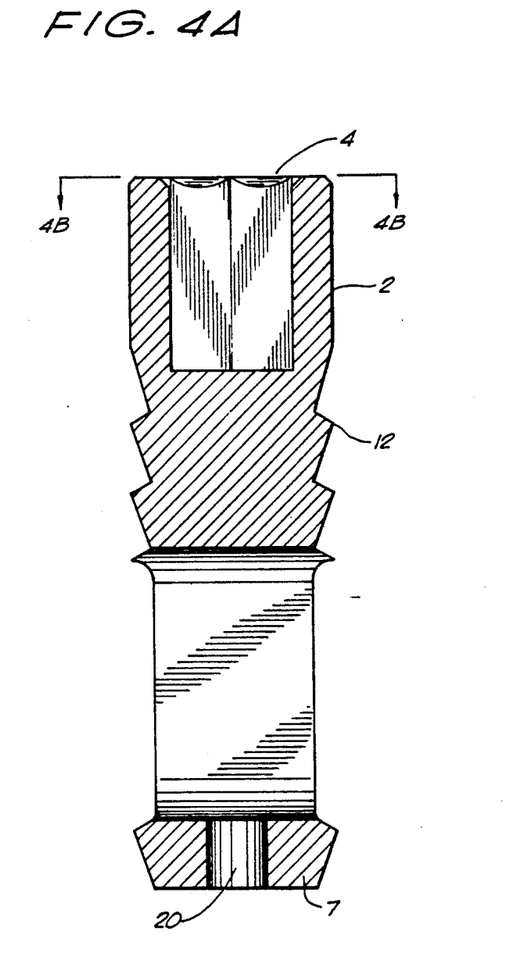
FIG. 4 is a cross-sectional view taken along axis A—A of FIG. 3.
Figure 4B:
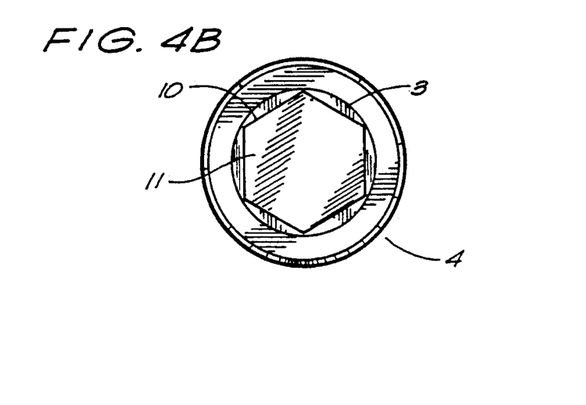
Figure 5:
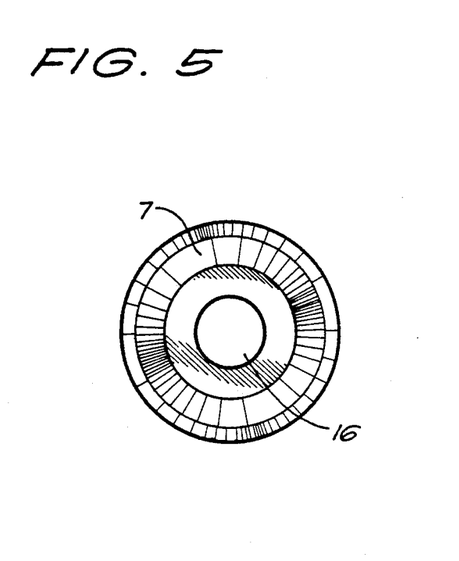
FIG. 5 is a bottom view of said implant body (FIGS. 1 and 3)

As can be seen, the impacted form of the implant body (1) (as shown in FIGS. 3 and 4) is similar to that of the screwed implant (as shown in FIGS. 1 and 2). The implant body (1) as illustrated in FIGS. 1 or 3 may be combined with a non-resilient implant head well known from the practitioners and composed for instance of conventional metallic false-stumps of truncated form that are screwed in said implant body (1).

However, in the preferred embodiment of the invention, said implant body (1) is combined with an implant head (9) as illustrated by FIG. 9, and is provided with at least two shock-absorber units (10a-11c).

With respect to the screwed and self-cutting implant, said implant body (1) is settled immediately and mechanically within said implantary osseous seating. Wellknown in the previous art are implant bodies including two features such as external threading and home screwing. A drawback involved is the very significant surface electric differential induced between the upper section of the whorl and its lower section which is likely to generate corrosion phenomenons altering the cellular equilibrium. In order to overcome such drawback, the invention provides an implant body (1) wherein the said cylindrical tube includes an external threading the thread pitch of which is as large as 1.25 mm at least. This results in the phenomenon of surface differential ventilation being reduced significantly or eliminated.

In the preferred embodiment of the invention (as shown in FIGS. 1 and 2) the said cylindrical tube (2) external threading (5) begins at least 2.3 mm under the upper opening (4) of said cylindrical tube (2) so as to form a smooth external upper portion (15) the surface finish thereof being high polished.

Such said non-threaded upper external portion (15) is slightly flare shaped upwards in order to facilitate additional blocking of the said implant body (1). Owing to the risk of imperfection on drilling, the entire upper portion of the implantary seating or osseous anchoring cavity of implant can be overdimensioned.

Figure 6:
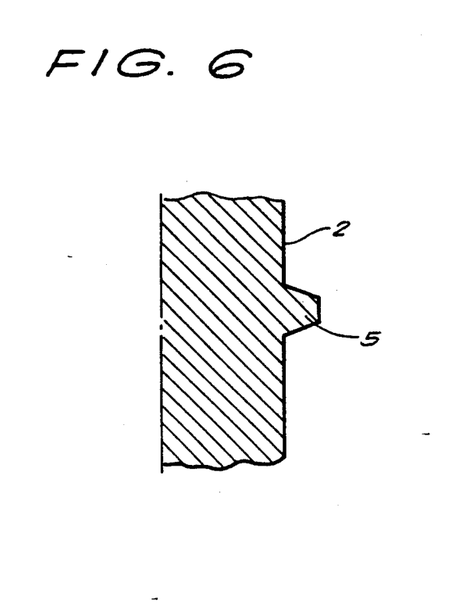
FIG. 6 is a detailed view of the external threading whorls of the implant body screwed and self-cutting according to the invention.

Similarly, in order to improve the implant mechanical primary attachment, the said external threading (5) is slightly overdimensioned with regard to said implantary seating dimensions as obtained by the means of the twist drill to be later described. Finally, such said external threading (5) is comprised of whorls as illustrated in FIG. 6. The cone point is truncated so as to form a vertical edge thus avoiding the building-up of electrical peaks likely to disturb the biological environment.

Figure 7:
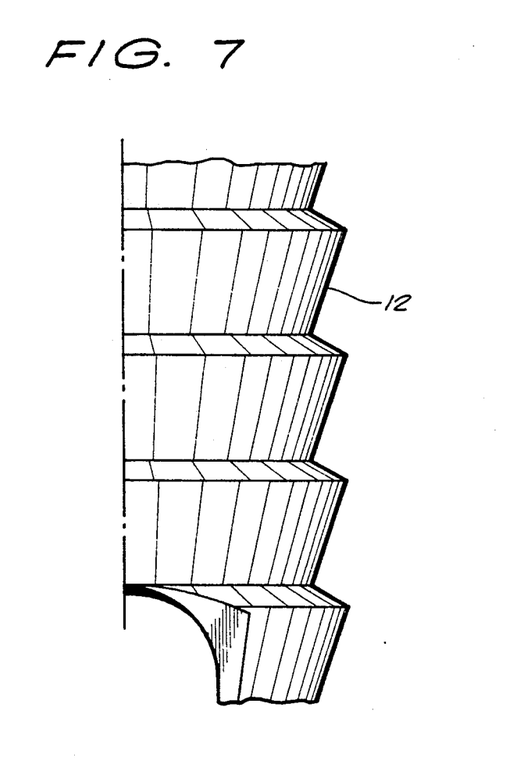
FIG. 7 is a detailed view of the series of shoulders lying on another of the implant body impacted according to the invention.

Under impacted design of FIGS. 3 and 4, the series of shoulders lying on another (FIG. 7) shows a definite relief. As a matter of fact, each shoulder comprises on one hand a very short heel directed upward and intended to prevent the implant loosening and on another hand a much larger downward heel which will transmit the mastication loads over a larger osseous volume.

All the features such as above described contribute to achieve a very close contact between the osseous surface and said implant body so that a bio-integration occurring at bone/implant interface is obtained.

In a preferred embodiment of the invention, said implant body (1) is made from titanium of commercially pure type or from any other bio material having biological, chemical and physical properties compatible with the biological environment.

Furthermore, another object of the invention is to ensure a "physiological mobility" to the implantable system as intended to support a dental prosthesis. To do so, the structure of said implant body (1) should not only be designed so as to allow an efficient integration of said implant body (1) within the jawbone, but additionally a resilient head (9) shall be provided to support the prosthesis. To this end, the said resilient implant head (9) according to the invention is composed of one cylindrical basis (17) the lower portion of which is threaded (FIG. 9). The cylindrical basis (17) is to be screwed in said internal threading (3) of said implant body (1) and a cylindrical stump (18) for supporting the prosthesis with two shock-absorbing units (10a, 11a) at least being provided atop thereof.

In order to be efficient, such said resilient implant head (9) should act as a true occlusive stress absorber at the time of mastication.

More precisely, referring to FIG. 9, the said resilient implant head (9) is provided with a first shock-absorbing element (10a) which is composed of a reversed truncated cone ring surrounding the non-threaded cylindrical portion of said cylindrical basis (17). A second shock-absorbing element (11a) composed of one ring is provided above said cylindrical stump (18) of the prothesis support, thus surrounding the head of the adjusting screw (19) which is a portion of the prosthetic suprastructure. The adjusting screw (1a) is so screwed in the internal threading of said cylindrical stump (18).

Accordingly, the occlusive stresses shock-absorbing effect is achieved above the bone through said shock-absorbing elements (10a, 11a) prior to occurring in the jawbone. Such said shock-absorbing elements (10a, 11a) are variable in width and consistency on account to the patient's masticatory pressure and the tooth to be replaced.

Measurements of the patient's proper masticatory pressure will be made on mouth site to determine the material specific quality and thickness that are the most appropriate for obtaining the best shock-absorbing performance. Similarly, the height of said cylindrical stump (18) for supporting the prosthesis will vary according to the prosthetic heights to be achieved. Such said shock-absorbing elements (10a, 11a) are made from P.C.T.F.E. (polychlorotrifluoroethylene) or any other compressible materials of selected thickness and compressibility which approximate the physiological mobility of a natural tooth.

Such said head (9) according to FIG. 9 is made preferably from titanium and can be adapted to any other type of implant body providing that said implant body is implemented according to the above mentioned procedure i.e. by screwing.

A further object of the invention is to provide a rotary device to achieve an implantary seating thoroughly cylindrical for said implant body (1) accomodation.

Figures 10A, 10C, 10D, 10E:
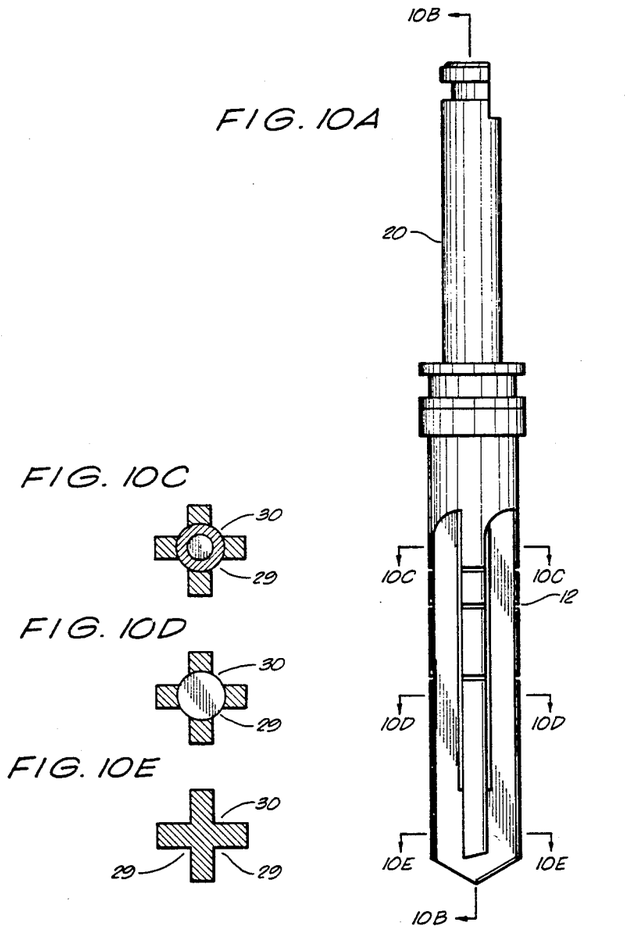
Figure 10B:
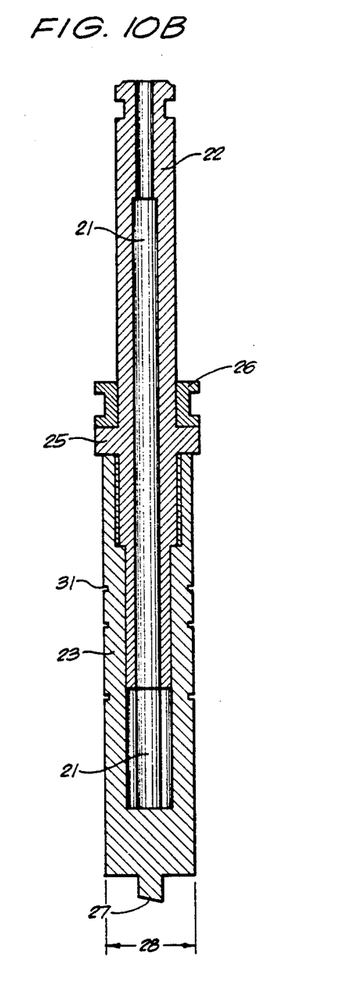

As shown in FIG. 10, the present invention provides a rotary device comprising a twist drill (20) including an internal irrigation channel (21) the so-called cruciform ratchet borer with internal irrigation.

More precisely, such said twist drill (20) is composed of a chuck (22) the lower portion of which is coated with a cylinder (23) recessed so as to form a cruciform cross-section for achievement of a thoroughly cylindrical osseous seating.

Moreover, such said chuck (22) includes lengthwise, internally, an irrigation channel (21) opening inside the punched section (24) of said cylinder (23).

The lower portion of said recessed cruciform cylinder (23) is ended by chisel faces (27-28) of which the sloping position allows bone cutting.

Thus, the resulting chips ascend to the two diametrical quadrants (29) while the cooling agent is flowing inside the two others (30).

Such said internal irrigation channel (21) is advantageous in that when such said rotary device is implemented for drilling the cylindrical implantary seating, a cooling agent which is free from germs and cooled to approximately 2°-3° C. is sent into said irrigation channel (21) opening into the punched section (24) of said cylinder (23).

In this way, the osseous cells overheating is eliminated, which prevents non-reversible lesions to occur and, consequently, an osteogenesis can be made inside said recessed portion (6) of said implant body (1) accomodated in said implantary seating by a screwing operation.

The blade chisel face that form the cruciform section of the twist drill (23) body shows drill marks corresponding to implant length. However, in the event of the recess portion (23) clogging, owing to the design in two portions of the twist drill, the latter will be disassembled, cleaned and returned to operation. Said twist drill can be covered with a packing material (26) received in the chuck (22). Such packing material is used to absorb the drilling vibrations.

Finally, another object of the present invention is to provide an operating method for the above-described implantory seating comprising the following steps.

Figure 8:
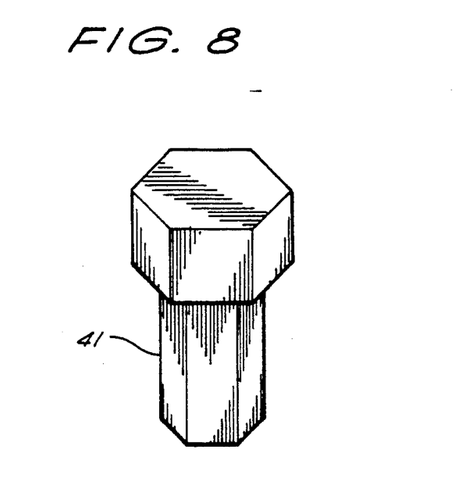
FIG. 8 is a perspective view of the male hexagon device according to the invention.

The internal threading (3) communicating with the upper opening (4) of the implant body (1) in association to an hexagon socket mechanism (10) is advantageous in that the implant body (1) fitting within the jawbone can be effected in a simple manner. As a matter of fact, a positioning device composed of a male hexagon device (41), as illustrated in FIG. 8, needs only to be incorporated into said internal threading (3) for implant body fitting within the jawbone by using an appropriate ratchet handle and then the male hexagon device (41) is removed by simply drawing it upwards.

Furthermore, the ratched handle chuck for implant body fitting exhibits a mark for the recessed portion (6) to be orientated to intra-osseous/mesio-distal position in order to facilitate the osseous restructuration and vascularization.

Preferably, the male/socket hexagon system (10, 11) according to the invention is asymmetrical.

Accordingly, the device for prothetic reconstruction to be screwed or sealed into the asymmetrical socket hexagon (10) is returned to its correct position on handling.

Moreover, another aspect of the present invention lies in the implant body's ability to be impacted (FIG. 3) instead of being screwed (FIG. 1).

As a matter of fact, according to FIG. 1, the implant body (1) is surrounded by an external threading (5) composed of a thread pitch for implant body screwing in the jaw. However, screwing of the implant body (1) requires the presence of the bone in a sufficient amount.

Owing to this, in the case of where the jawbone is not large enough, the external threading (5) is replaced by a series of shoulders lying upon another (12).

The implant is then fixed into the jawbone through impacting by using said shoulders relief (12). Thus the biasing of the implantary seating walls is decreased which prevents embrittlement of the jawbone.

Further, another object of the present invention is to provide a resilient implant head that can be used within the implant procedure applicable to entirely toothless patients.

Figure 11:
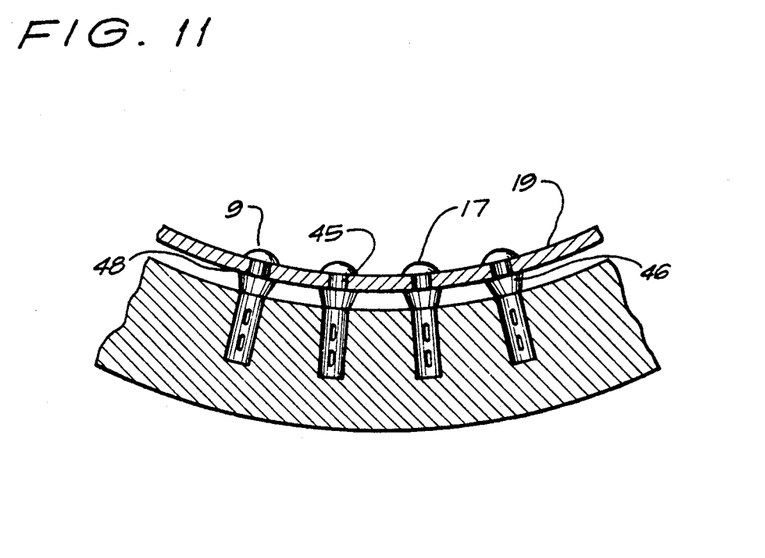
FIG. 11 is a front view of an implantable system relevant to the method applied to entirely toothless patients.

To this end, the resilient implant head (9), such as illustrated in FIG. 11, is composed of a screw (45) the low threaded section of which is inserted in the internal threading (3) of implant body (1). The high smooth section of said screw (45) is partly covered with a shock-absorbing ring (46) so as to arrange between said screw (45) and the top (48) of said shock-absorbing ring (46) a space used for holding of a bar (19) integral with all existing implants.

In this way, the associated bar (19) is supported by the shock-absorbing rings (46) of all implants, owing to which a physiological mobility similar to that of dental organs can be achieved.

Consequently, the present invention further relates to an operating method of such said resilient implant head (9) adapted to the implant procedure applicable to entirely toothless patients wherein a bar which is integral with all the existing implants and is used to form a link therewith, is locked both by the shock-absorbing ring (46) and the screw head (15) of each resilient implant head (9).

Figure 12:
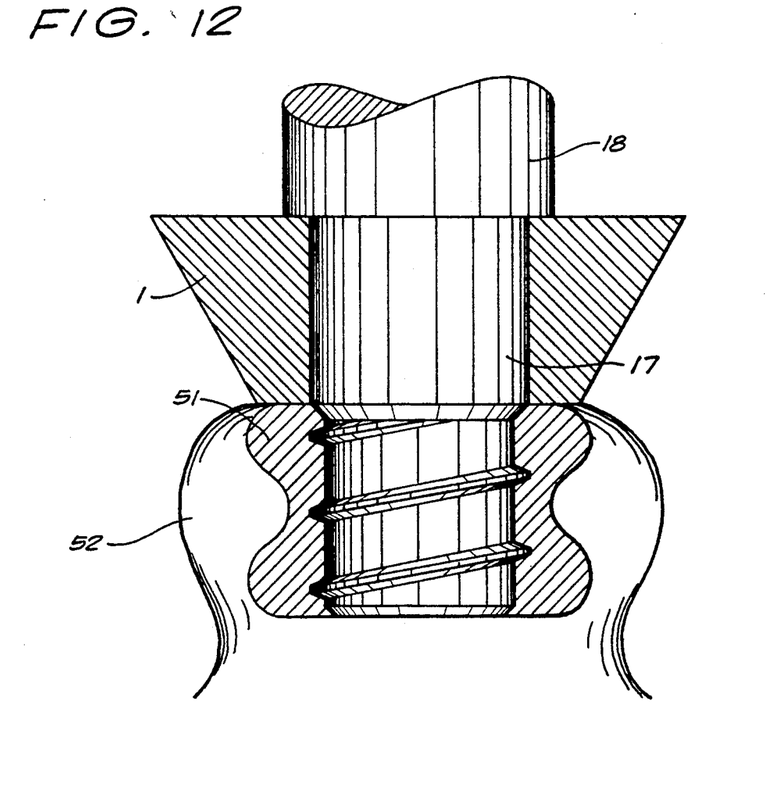
FIG. 12 is a view of a juxta-osseous implant according to another embodiment of the invention.

In another embodiment of the invention, said resilient implant head (9) can be used with the juxta-osseous implant procedure. To this end, said cylindrical threaded basis (17) is locked according to FIG. 12 in a prefabricated metal ring (51) which itself is embedded within the metal volume of the juxta-osseous implant (52) during the preparation at the dental prosthesis laboratory. It is obvious that the invention is not limited to the above described embodiments to which many changes can be brought within the scope of the invention.

What is claimed is:

1. An implantable device for supporting a dental prosthesis comprising an implant body shaped as a cylindrical tube having an internal threading at an upper end of said cylindrical tube, said internal threading for receiving an implant head therein, an asymmetrical hexagonal socket formed in said cylindrical tube below said internal threading, a recessed portion extending for greater than half of a length between a bottom of said internal threading and an apical portion of said cylindrical tube, said recessed portion defining two communicating openings arranged oppositely along said tube, said recessed portion having vertical edges, said cylindrical tube having external threading extending along a portion of a length thereof, said vertical edges of said recessed portion forming side faces with said external threading adjacent said recessed portion, said external threading having projecting whorls with a truncated outer surface.

2. An implantable system as recited in claim 1, wherein said external threading of said cylindrical tube has a thread pitch equal to 1.25 mm at least.

3. An implantable system as recited in claim 1, wherein said external threading has a diameter larger than that of an implantary seating.

4. An implantable system as recited in claim 1, wherein said external threading of said implant body comprises a series of shoulders lying upon one another.

5. An implantable system as in claim 1, wherein a decompression opening is formed through the apical part of said implant body and provides a communication between the recessed portion of said implant body and an osseous cavity.

6. An implantable system as recited in claim 1, wherein said implant body is connected to a resilient implant head including at least two shock-absorbing elements.

7. An implantable system as recited in claim 6, wherein said resilient implant head comprises a cylindrical base having a threaded lower part screwed in said internal threading of said implant body, said implant head has an upper part with a cylindrical stump.

8. An implantable system as recited in claim 7, wherein said implant head includes a first shock-absorbing element comprised of a reversed truncated ring, a second shock-absorbing element is comprised of a ring provided above said cylindrical stump, said second shock-absorbing element surrounding a head of an adjusting screw.

9. An implantable system as recited in claim 8, wherein said shock-absorbing elements are made from compressible and biocompatible polychlorotrifluoroethylene.

10. An implantable system as recited in claim 6, wherein said implant body and said implant head are made from titanium.

* * * * *